(12) United States Patent (10) Patent No.: US 8,480,617 B2
Lenzner et al. (45) Date of Patent: Jul. 9, 2013

(54) INJECTION DEVICE AND AMPOULE UNIT

(75) Inventors: Benedikt Lenzner, Hildesheim (DE);
Stephan Theuer, Sehnde (DE); Bernd Störmer-Talleur, Hohenhameln (DE);
Dirk Schulz, Mannheim (DE)

(73) Assignee: Painless Tech GmbH, Hildesheim (DE)

( * ) Notice: Subject to any disclaimer, the term of this patent is extended or adjusted under 35 U.S.C. 154(b) by 287 days.

(21) Appl. No.: 12/096,740

(22) PCT Filed: Nov. 16, 2006

(86) PCT No.: PCT/EP2006/010990
§ 371 (c)(1),
(2), (4) Date: Nov. 24, 2008

(87) PCT Pub. No.: WO2007/065542
PCT Pub. Date: Jun. 14, 2007

(65) Prior Publication Data
US 2009/0157039 A1 Jun. 18, 2009

(30) Foreign Application Priority Data

Dec. 7, 2005 (DE) .......................... 10 2005 058 655
Dec. 7, 2005 (DE) .......................... 10 2005 058 656

(51) Int. Cl.
*A61M 5/30* (2006.01)
(52) U.S. Cl.
USPC .................. 604/72; 604/68; 604/69; 604/70;
604/82; 604/83; 604/85; 604/184; 604/231;
604/232; 604/233; 604/234; 604/235

(58) Field of Classification Search
USPC ................... 604/68–70, 72, 232–235, 82, 83,
604/85, 199, 184, 231
See application file for complete search history.

(56) References Cited

U.S. PATENT DOCUMENTS

| | | | | |
|---|---|---|---|---|
| 1,707,880 | A | * | 4/1929 | Sheets ........................... 604/125 |
| 2,459,875 | A | | 1/1949 | Folkman |
| 4,124,024 | A | | 11/1978 | Schwebel et al. .......... 128/173 H |
| 4,553,962 | A | | 11/1985 | Brunet |
| 4,713,060 | A | * | 12/1987 | Riuli ............................. 604/199 |
| 5,074,843 | A | | 12/1991 | Dalto et al. ..................... 604/68 |
| 5,137,516 | A | * | 8/1992 | Rand et al. .................... 604/136 |
| 5,435,076 | A | * | 7/1995 | Hjertman et al. ............... 34/296 |
| 5,822,958 | A | * | 10/1998 | Davis .............................. 53/551 |
| 5,891,086 | A | * | 4/1999 | Weston ........................... 604/70 |
| 6,258,068 | B1 | | 7/2001 | Kirchhofer et al. |
| 6,319,224 | B1 | | 11/2001 | Stout et al. |
| 7,056,300 | B2 | | 6/2006 | Alexandre et al. |

(Continued)

FOREIGN PATENT DOCUMENTS

CH 694483 2/2005
DE 20105183 U1 6/2002

(Continued)

*Primary Examiner* — Bhisma Mehta
*Assistant Examiner* — Larry R Wilson
(74) *Attorney, Agent, or Firm* — Seed IP Law Group PLLC (57) ABSTRACT

The invention relates to an injection device for the needle-free injection of a medium. Said injection device comprises an injector device and an ampoule unit, said ampoule unit comprising a base (4) holding the medium to be injected. Said base comprises a jacket (5) which exerts pressure on the base, and jacket completely enveloping the base in the longitudinal axial direction.

8 Claims, 5 Drawing Sheets

U.S. PATENT DOCUMENTS

| | | |
|---|---|---|
| 2003/0050596 A1 | 3/2003 | Alexandre et al. .............. 604/69 |
| 2004/0254526 A1 | 12/2004 | Weston |
| 2005/0013840 A1 | 1/2005 | Potter et al. |
| 2005/0154350 A1 | 7/2005 | Willis et al. |
| 2005/0192530 A1 | 9/2005 | Castellano |
| 2006/0224117 A1 | 10/2006 | Hommann et al. |

FOREIGN PATENT DOCUMENTS

| | | |
|---|---|---|
| DE | 10137961 A1 | 3/2003 |
| DE | 102 11 473 | 10/2003 |
| DE | 69928012 T2 | 7/2006 |
| EP | 0114145 A2 | 7/1984 |
| EP | 0 367 677 | 5/1990 |
| EP | 0 595 508 | 5/1994 |
| EP | 1762261 B1 | 3/2007 |
| GB | 2 404 865 | 2/2005 |
| WO | WO 96/15821 | 5/1996 |
| WO | WO 9615821 A1 * | 5/1996 |
| WO | 00/35520 A1 | 6/2000 |
| WO | 01/58512 A1 | 8/2001 |
| WO | WO 2005/021071 | 3/2005 |

* cited by examiner

INJECTION DEVICE AND AMPOULE UNIT

BACKGROUND

1. Technical Field

The subject matter of the present invention relates to an ampoule unit for an injection apparatus and an injection apparatus for the needle-free injection, in particular subcutaneous, intracutaneous, intramuscular, intra-articular, submucous injection, by means of an injector device and an ampoule unit.

2. Description of the Related Art

In the past 10 to 15 years, a large number of injection apparatuses for the needle-free injection of a medium have been developed; however, to this day, the injection apparatuses destroy the associated ampoule units, in which case it is sometimes not possible during application to prevent material particles along with the medium to strike or penetrate the skin at a high pressure, with high pressures and velocities frequently causing injury to skin and tissue.

An example is the device disclosed in DE 102 11 473 A1, in this case an ampoule for an injection apparatus for the needle-free injection of a medium into human or animal tissue, comprising an ampoule body, with a chamber disposed inside the ampoule body for holding the medium, with a nozzle for generating a high-pressure jet of the medium ejected from the ampoule, and a longitudinally movable plunger and a longitudinally movable stopper for sealing the chamber, with the ampoule body comprising a segment disposed at a distance from the nozzle and made of a material appropriate for the medium and a pressure-resistant segment disposed near the nozzle, with a circulating flow region that allows the medium to flow around the stopper disposed on the end of the pressure-resistant segment facing away from the chamber.

DE 695 08 104 T2 discloses a glass container for use as a needle-free injection capsule that has a hollow glass body, characterized in that compression means are provided to exert a compressive force on the hollow glass body, thereby making it possible for the container to withstand high pressure. However, the disadvantage of this type of design is that, during application, the glass very often splinters in the conically tapering anterior area of the ampoule, which leads to minor skin injuries during the application.

BRIEF SUMMARY

At least some embodiments of the present invention make available an appropriate injection apparatus and ampoule unit in which the disadvantages mentioned are eliminated or considerably reduced. In some embodiments, the device and ampoule unit provide needle-free injections of a medium through the skin with minimum injuries.

The injection apparatus according to the present invention for the needle-free injection of a medium comprises an injector device and an ampoule unit. The ampoule unit in turn comprises a base body for holding the medium to be injected and a jacket which exerts compressive forces on the base body. The jacket completely envelopes the base body in the direction of the longitudinal axis. Among other things, it is especially essential to some embodiments that, because the base body is completely jacketed along the longitudinal axis, the risk of glass breakage and, thus, of injury during the application is practically completely eliminated.

The advantage is that the compressive forces exerted by the jacket, at a minimum, compensate for the internal stresses that built up in the course of manufacturing the base body, since most base bodies are made of glass and, during the production of an ampoule-shaped glass base body, due to the different cooling rate from the outside to the inside, stresses that have a negative effect build up. Thus, when compressive forces are exerted on the base body to eject the medium to be injected, the probability of breakage and a detachment of base body particles is reduced, with a special advantage offered if the jacket exerts at least up to 100% of the compressive forces that build up during the injection on the base body, thereby ensuring complete compensation and thus a considerably lower risk of breakage.

The jacket is preferably shrink-fitted, applied by a casting method, by polymerization or by means of press-fitting onto the base body.

Shrink-fitting is performed by heating the jacket to an elevated temperature, for example, to +100° C., which causes the inside diameter to expand, thus allowing the base body to be inserted. On cooling, preferably to room temperature, the jacket contracts and clings to the base body, which causes the jacket to exert compressive forces onto the base body. The effect is the same if instead of heating the jacket, the base body is cooled, for example, in liquid nitrogen, or if the jacket is heated and the base body is cooled at the same time. In the casting process, the base body is coated with a low-melting metal alloy or a plastic material, for example, polyamide, by a spraying technique. In this case, for example, especially the base body can be mounted on a rotating mandrel and the alloy or the plastic material sprayed on at the same time by means of a spraying device. If polymerization is used, a plastic material is sprayed onto the base body in a mold; for example, the base body is located in an injection mold and a suitable plastic material is injected into the mold, i.e., into the hollow space between the inside wall of the injection mold and the base body, and thus onto the base body. If press-fitting is used, the base body is inserted under pressure into a jacket, in particular one made of a plastic material or a metal alloy or a metal, and due to fact that the inside dimension of the jacket is slightly smaller than the outside diameter of the base body, high pressure is built up and exerted onto the base body.

As practical experience has demonstrated, the jacket can be made of a plastic material or a metal, the base body is made of glass (e.g., borosilicate glass), since in this type of glass, the ability of small glass particles to migrate, i.e., the ability of glass components to detach themselves, thereby leading to contamination, is very low, and the jacket is made, in particular, of polyamide, a bonded fabric, especially of plastic materials with glass fibers and carbon fibers, or an MCP alloy. The MCP alloys are low-melting metal alloys containing in particular Bi, Sn and In, for example, MCP 96 and MCP 137 alloys of HEK GmbH, Kaninchenborn 24-28, D-23560 Lubeck, Germany.

Thus, by shrink-fitting or using a casting process, polymerization or press-fitting to apply polyamide, a bonded fabric or an MCP alloy, materials highly shrinkable on cooling, preferably to room temperature, onto the base body preferably made of borosilicate glass and by means of the resultant shrinkage, which causes high compressive forces to be exerted. The base body is sufficiently pressurized and, thus, the risk that the material of the base body will break when high pressure is exerted in order to eject the medium to be administered is avoided.

As a result of shrink-fitting or the casting process, polymerization or press-fitting, the compressive forces that built up are very high, and therefore, the resistance to compressive forces during application cannot be compared to that of glass ampoules enveloped by a conventional plastic material (such as disclosed in DE 102 11 473 A1).

In this context, it is useful if the injection apparatus comprises an injector sleeve for the needle-free injection of a medium, an injector device, a spring activation element for ejecting the medium to be injected, with the injector device, when in the spring-loaded state, set up in such a manner that, with respect to the tension of the spring activation element, only the spring activation element, the activating element, the locking element and the thrust-bearing device are exposed to the spring tension force, while the injector sleeve is not exposed to the spring tension force because the thrust-bearing device is independent of the injector sleeve. Thus, in contrast to the prior-art, it is not necessary for the injector sleeve to be made of relatively expensive metals or fiber-reinforced plastic materials since according to the present invention, the injector sleeve is no longer exposed to the spring tension force.

In this context, it has been found extremely useful in practice if the activating element tensioned by the spring activation element is/can be releasably arrested by a locking element and the forces generated by the spring activation element are absorbed by a thrust-bearing device. The elements, i.e., the spring activation element, the activating element, the locking element and the thrust-bearing device, thus form a "closed system" which, with respect to the forces, is pre-tensioned and which is independent of the other parts of the apparatus.

Since the locking element requires little space and can have a slender shape when viewed in the direction of the longitudinal axis, it is useful if the locking element is a pin-shaped element acting on the activating element to lock it. In this context, it is useful if the locking element is designed in the form of a lever, thereby making it possible for the releasing forces to be appropriately adjusted by ensuring the desired free movability via the leverage, and/or if the locking element locks the activating element in an undercut section.

In this context, it is also useful if a releasing element for the activating element tensioned by means of the spring activation element can be activated substantially in the direction of the injection of the medium to form a favorable application angle relative to the skin surface during the injection through the skin, depending on the medical indication, and, thus, to be easily activated. In this context, it is also useful if the activating element can be released by swiveling or rotating the locking element, in which case it is furthermore useful if the releasing element has a wedge-like shape so that, when the releasing element is activated, it engages the locking element in the direction of the injection.

It is furthermore of optimum advantage if the ampoule unit can be mounted onto and/or be removed from the injector device, in particular if the ampoule unit can be friction-mounted on the injector device to bring the injection apparatus into a pre-injection state, thereby moving a potentially sensitive medium to the injector device just shortly prior to application and subsequently injecting the medium without the risk of decomposition processes developing prior thereto. Thus, by assembling the injector device and the associated ampoule units to form the injection apparatus according to the present invention, it is possible to administer different media using the same injector device.

In this context, it is useful if the mounting and removing is implemented by means of a screw thread or a ring-shaped click-stop connection, which are embodiments that have been shown to be useful in practice.

In addition, it is useful if the ampoule unit is prefilled with the medium to be injected, in particular so as to be nearly or completely free from gas, to ensure that during injection, pressure is not lost due to bubble formation or that potentially present air or other gases, for example, nitrogen, are administered as well, which could lead to dangerous embolisms in the body.

To ensure that the injection apparatus is not accidentally released, the injection apparatus preferably comprises a safety element to protect the releasing element, the releasing element having the shape of a ring, and in particular, the injector device and/or the releasing element comprise(s) a groove for receiving the safety element so that the releasing element is protected during transport and/or against accidental release by simply inserting or removing the safety element, i.e., by pulling it off or attaching it.

The ampoule unit preferably comprises a longitudinally movable stopper element which seals off a surface along the longitudinal axis and which, during injection, preferably ejects the medium from the ampoule unit.

The ampoule unit is preferably friction-mounted to an injector device, in particular the injector device according to the present invention, to bring it into a pre-injection state, with the mounting and removing being implemented by means of the screw thread or a ring-shaped click-stop connection.

It is also useful if a nozzle discharged from the medium injected is disposed on the axially longitudinal end of the ampoule unit, the nozzle made in particular of steel—especially of alloy 1.4301 or 1.4435, which is an austenitic non-rusting steel known in short as X5CrNi18 10 (AISI 304), also commonly known under the trade name V2A, with the chemical composition $C \leqq 0.07\%$, $Si \leqq 1.0\%$, $Mn \leqq 2.0\%$, $Cr=17$ to $20\%$, $Ni=8.5$ to $10\%$, or an austenitic nonrusting steel known in short as X2CrNiMo18-14-3 (316 L), also known under the trade name SUPRA, with the chemical composition $C \leqq 0.03\%$, $Si \leqq 1.0\%$, $Mn \leqq 2.0\%$, $Cr \leqq =17.0$ to $18.5\%$, $Mo \leqq =2.5$ to $3.0\%$, $Ni=12.5$ to $1500\%$—and having one or at least two discharge openings to obtain a relevant medium- to high-pressure jet during administration. In case of several discharge nozzles and the resultant larger application surface, the kinetics can be adjusted as a function of the indication.

It is also useful if the axially longitudinal end of the ampoule unit as the discharge end for the medium to be injected is covered by a cap so as to ensure sterile conditions until shortly prior to application.

It is also useful if an elastic sealing element is disposed between the base body and the nozzle, in particular one made of silicone, so as to prevent partial medium slips between the base body and the steel nozzle during application, which due to a drop in pressure and/or leakage would lead to considerably inferior applicability or complete loss of applicability.

It is also useful if in the injection apparatus and the ampoule unit, the nozzle and nozzle screw joint form a snug sealing fit, in particular if the nozzle screw joint, when mounted and viewed in the longitudinal section, is conically tapered on the inside and, again as viewed in the longitudinal section, conforms to outside surface of the conically tapering nozzle since, in this relatively simple, yet effective manner, excellent leakproofness is provided and, thus, the nozzle is seated in the nozzle screw joint ensuring a seal and an excellent fit. In addition, because of the snug fit formed, the nozzle is oriented as desired and thus lies close to the sealing element so as to seal it as desired. In this manner, both orientation and leakproofness are implemented.

It is also useful if a plunger rod driving the stopper element is hollow and, in addition, if the stopper element has a material recess corresponding to the hollow space in the stopper element, since this makes it possible to fill the pharmaceutical agent subsequently applied conveniently into the base body in that a syringe-like applicator is inserted in a conventional bottling station through the hollow channel of the plunger rod and, through the material recess in the stopper element, to subsequently transfer a certain quantity of a suitable pharmaceutical agent into the base body and subsequently pinch the hollow plunger rod in one place or in several places, for example, and especially after removing the needle-shaped applicator, and thereby to fill the ampoule to be nearly or completely free from gas.

It is also useful if the stopper element after its release, i.e., especially during the injection of a certain pharmaceutical agent through the skin, detaches itself from the plunger rod as the plunger rod is retracted, thereby ensuring that undesirable multiple use is avoided. For example and in particular, such a design can be implemented by making the anterior part of the plunger rod strike against the posterior part of the stopper element, without being protected by undercutting the elements on retraction, so that the plunger rod can freely move toward the back without taking along the stopper element.

It is also useful if after activating the releasing element, the releasing element remains in the injector sleeve, in this manner avoiding undesirable multiple activations. This can be implemented for example and in particular in that on release, the locking element detaches itself from, so-to-speak "drops off," an undercut section of the activating element and lies loosely inside the injector.

It is also useful if the plunger rod is pinched in at least one place, preferably in two places, so as to provide a seal.

In contrast to cannulas of conventional syringes which have been in contact with tissue, blood, blood components or other infectious material, the injection apparatus and the ampoule unit need not be disposed of as hazardous waste.

The features and advantages of the injection apparatus according to the present invention described above relevant to the ampoule unit obviously also pertain to the ampoule unit as such.

BRIEF DESCRIPTION OF THE SEVERAL VIEWS OF THE DRAWINGS

Using an example, the invention will be described in greater detail based on the figures below.

DETAILED DESCRIPTION

Figure 1:
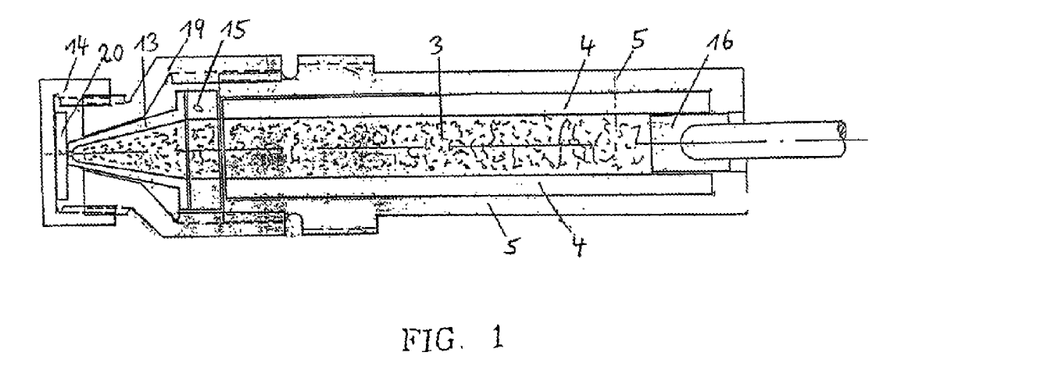
FIG. 1 shows a schematic representation of a cross-sectional view through a first embodiment of an ampoule unit according to the present invention.

FIG. 1 shows a schematic representation of cross-sectional view of an ampoule unit 2 which has a stopper element 16 (with a plunger rod as tentatively indicated) on one of its axially longitudinal ends. On the other axially longitudinal end of the jacketed 5 base body 4 which is filled with a medium 3 and which, in the direction of the longitudinal axis, is completely enveloped by the jacket 5. A sealing element 15 made of silicone is disposed between the steel nozzle 13 and the base body 4 and jacket 5. The steel nozzle 13 is mechanically attached so as to seal off the medium in a friction-locked and form-fitting manner by a nozzle screw joint 19. At the discharge end of the steel nozzle 13, a cap 14 is screwed on, with a cap seal 20 being disposed (for reasons of sterility) between the inside wall of the cap 14 and the discharge end of the steel nozzle 13. Prior to the injection, the ampoule unit 2 is attached to, in particular screwed onto, an injector device 1 so that, after cap 14 and cap seal 20 have been removed and the ampoule unit has been positioned on a specific area of the skin, the medium 3 can be applied by moving the stopper element in the direction of the longitudinal axis at least partially from right to left by means of the driven plunger rod.

The nozzle 13 is oriented so as to be centered in the longitudinal direction via the snug fit formed with the inside wall of the nozzle screw joint 19 and, thus, lies close to the sealing element 15 to provide a seal so that on application, the medium 3 can be applied without loss and in a targeted manner.

Figure 2:
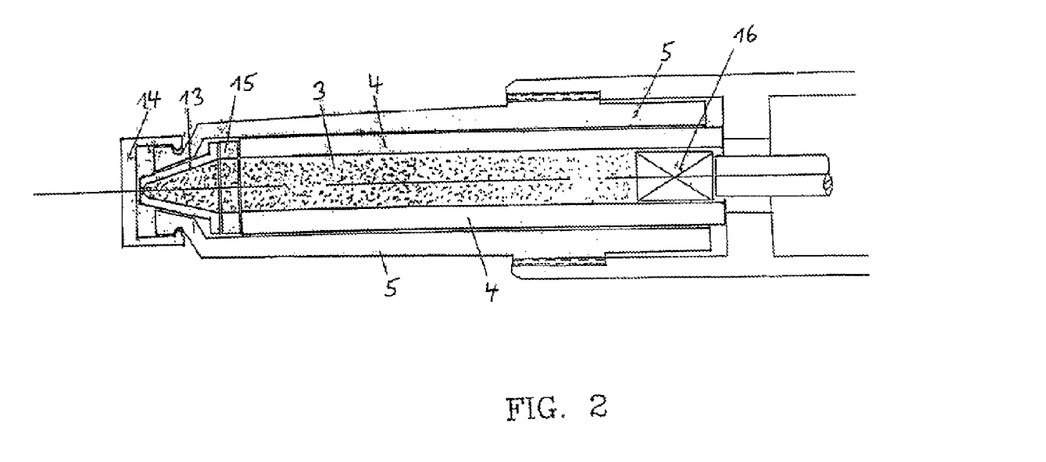
FIG. 2 shows a schematic representation of a cross-sectional view through a second embodiment of an ampoule unit according to the present invention.

FIG. 2 shows a variation of the embodiment of the ampoule unit 2 according to the present invention shown in FIG. 1, with the difference that instead of a nozzle screw joint 19, the jacket is designed so that the steel nozzle 13 lies close to the inside walls of the jacket 5 in a friction-locked and form-fitting manner and, thus, forms a snug fit. Another difference is that the cap 14 does not have an additional cap seal and that the cap cannot be screwed off but is instead pulled off.

Based on FIGS. 1 and 2, the person skilled in the art can clearly see that in the direction of the longitudinal axis, the base body 4 is completely enveloped by the jacket 5.

Figure 3:
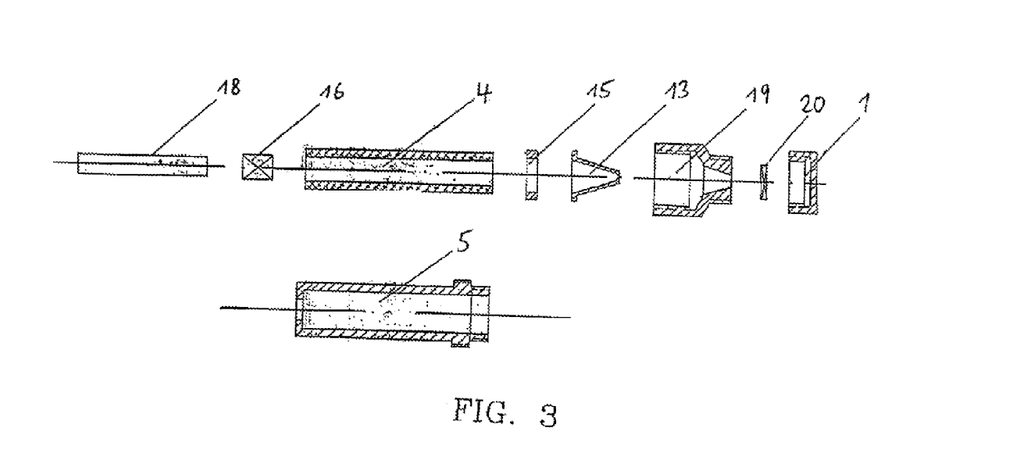
FIG. 3 shows an exploded cross-sectional view of an ampoule unit shown in FIG. 1.

In FIG. 3, the ampoule unit 2 seen in FIG. 1 is again shown in an exploded cross-sectional view to once again clearly illustrate the individual components, i.e., the plunger rod 18 that drives the stopper element 16, the stopper element 16 that can be moved inside the base body 4 in the direction of the longitudinal axis, the base body 4 which holds the medium 3, the jacket 5 which envelops the base body 4, the seal 15, preferably made of silicone, which ensures leakproofness between the steel nozzle 13 and the base body 4 and jacket 5, the steel nozzle 13 having a tiny discharge opening and thus producing a medium- to high pressure jet when the stopper element 16 is moved, the friction-locked and form-fitting attachment of the steel nozzle 13 and the sealing element 15 to the base body 4 and the jacket 5 by means of the nozzle screw joint 19, and the cap seal 20 providing an additional seal and finally the associated cap 14, both of which, for reasons of sterility, are not removed until just prior to application.

Figure 4:
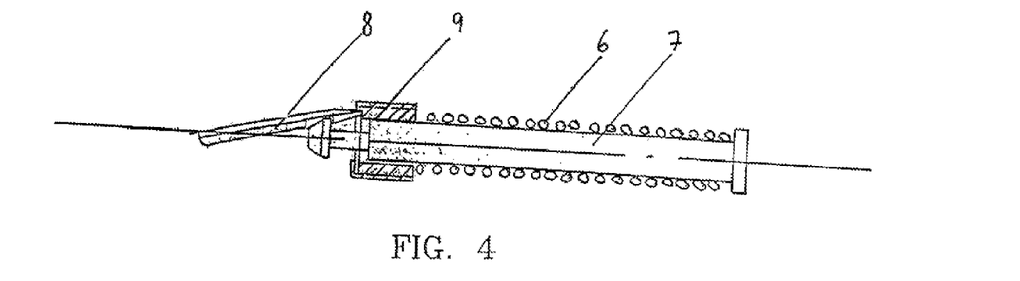
FIG. 4 shows a schematic cross-sectional view of the pre-tensioned "closed system" in an injector device of the injection apparatus according to the present invention.

FIG. 4 shows a schematic cross-sectional view of the elements forming the pre-tensioned closed system in the injector device of the injection apparatus according to the present invention, with the activating element 7 tensioned via the spring activation element 6 releasably locked via locking element 8 by means of a material recess, with the forces generated by the spring activation element 6 absorbed by a thrust-bearing device 9. These four elements constitute the pre-tensioned "closed system."

Figure 5:
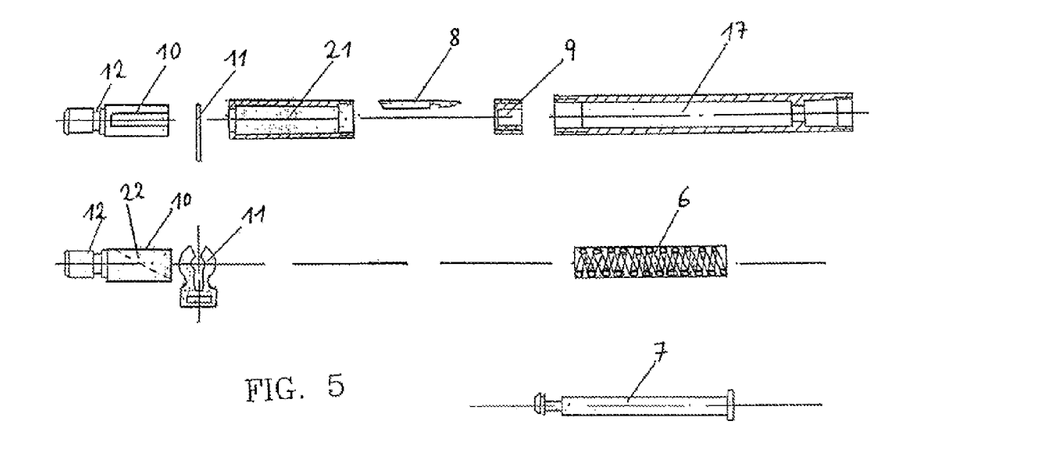
FIG. 5 shows a schematic exploded cross-sectional view through an injector device of the apparatus according to the present invention with a spring-tensioned injector.

In FIG. 5, the structural design of the injector device 1 of the injection apparatus according to the present invention is shown in an exploded cross-sectional view. A stem-like releasing element 10 comprises a groove 12 for receiving a semicircular safety element 11 for locking and preventing an accidental release, for example, during transport, with a pin-shaped locking element 8 with a material recess disposed in a cover cap 21 of the injector device 1. The locking element 8 is secured on the thrust bearing so that when the releasing element 10 and, thus, its inside wedge 22 are moved in the longitudinal direction, the wedge engages the locking element 8, and by way of the leverage and the swivelability and rotatability, the right end of the locking element 8 facing the thrust-bearing device 9 unlocks and releases the left end of the activating element 7 so that the activating element, due to the pre-tensioned spring activation element 6 is moved in the longitudinal direction to the right and thus a plunger rod of a mounted ampoule unit 2 according to the present invention is also moved to the right, thereby ejecting the medium from the base body 4 of the ampoule unit 2.

The activating element 7 is moved inside an injector sleeve 17 of the injector device 1.

Figure 6:
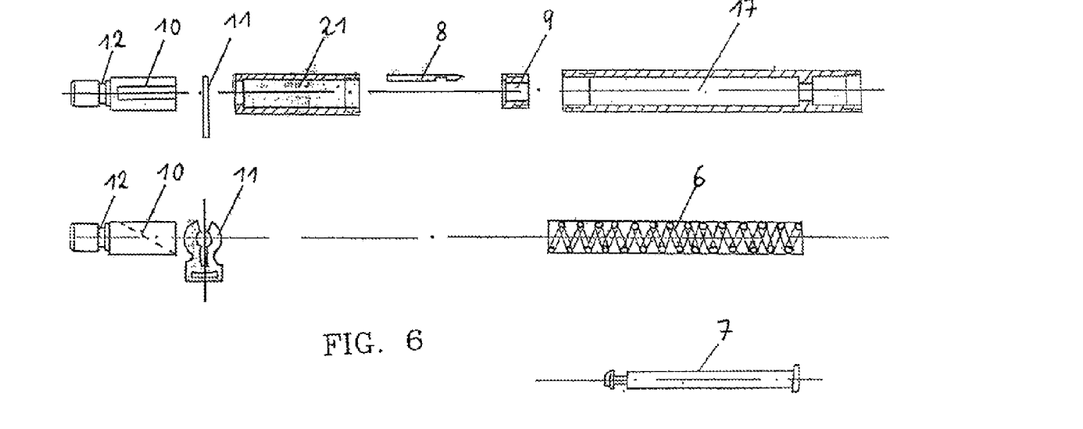
FIG. 6 shows a schematic exploded cross-sectional view through an injector device according to the present invention in the nontensioned state.

FIG. 6 shows the embodiment of an injector device of the injection apparatus according to the present invention seen in FIG. 5, but in a nontensioned state.

Figure 7:
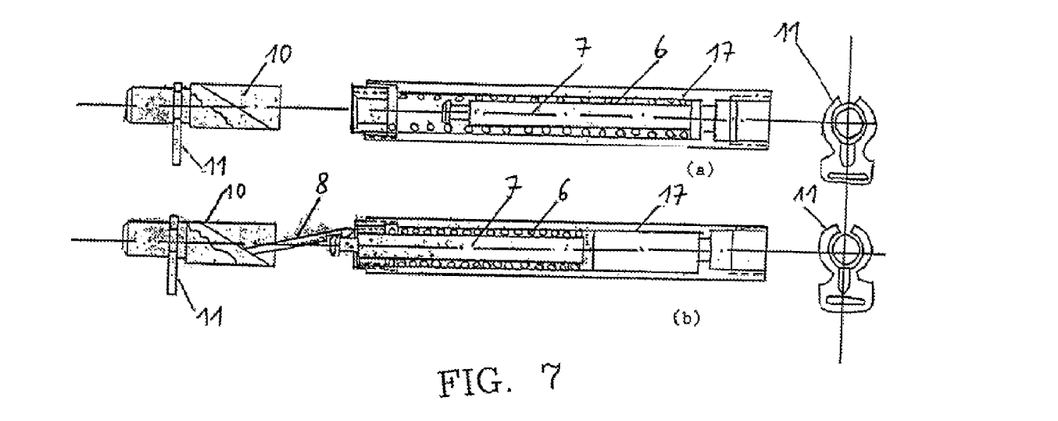
FIGS. 7a and 7b show the basic triggering principle for injecting a medium in the injection apparatus according to the present invention.

To further clarify the invention, FIGS. 7a and 7b once more explain the functional relationship already discussed in FIGS. 5 and 6, with the injection apparatus shown in FIG. 7a non-tensioned and that shown in FIG. 7b tensioned.

Figure 8:
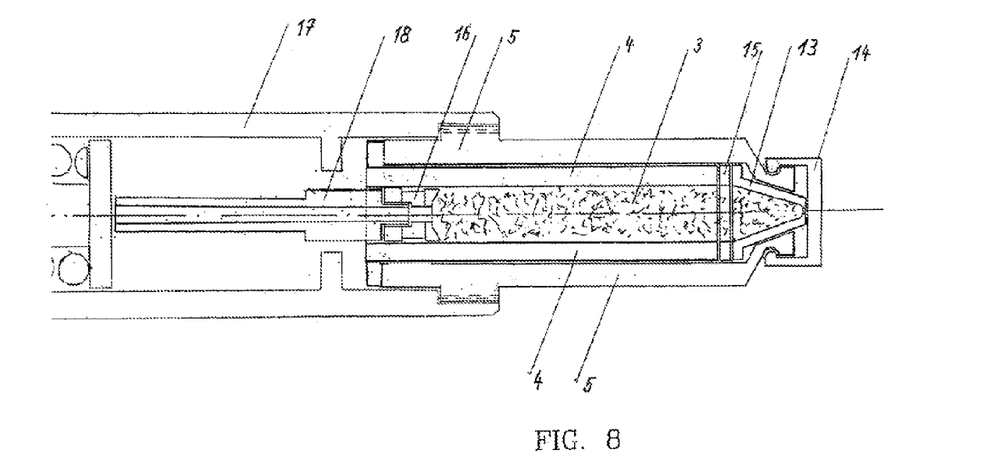
FIG. 8 shows a schematic cross-sectional view through another embodiment of an ampoule unit according to the present invention.
Figure 10:
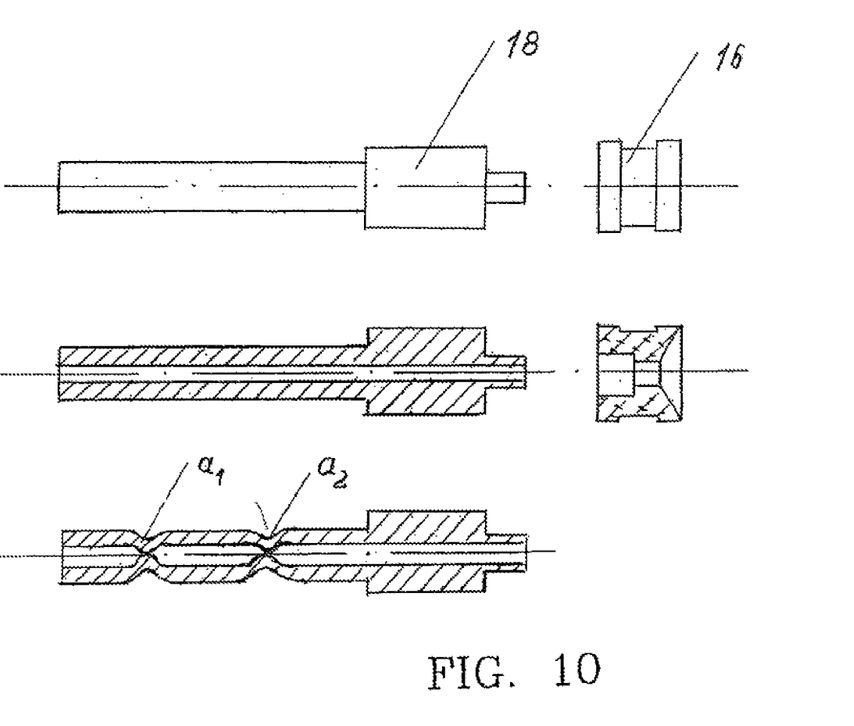

FIG. 8 shows a cross-sectional view of yet another embodiment of the ampoule unit according to the present invention in which a base body 4 made of borosilicate glass is completely jacketed in the direction of the longitudinal axis by a jacket 5 extending along the entire direction of the longitudinal axis, with the anterior end of the base body 4 lying close to a disk-shaped sealing element 15, thereby providing a seal, which disk-shaped sealing element in turn lies close to a nozzle 13 also providing a seal. The nozzle 13 as such engages and thus seals the conically tapering part of the inside wall of the nozzle, thereby preventing leakage of the medium 3 of the solution injected and contained in the base body 4 by way of the abutment created by the resultant snug fit as a result of the sealing effect of the sealing element 15. The nozzle 13 made of a metal is detachably closed by means of a cap 14 which engages in/attaches to undercut sections disposed on the anterior portion of the jacket. On the posterior axially longitudinal end of the base body 4, a stopper element 16 made of silicone is disposed in the direction of the longitudinal axis so that, due to the reversible deformability of the silicone materials, a seal is also formed in this direction along the inside glass walls of the base body 4 during the axially longitudinal movement to empty the base body 4. The stopper element 16 is driven by a hollow plunger rod 18 which comes to a stop, with the hollow space in the plunger rod 18 corresponding to a material recess of the stopper element 16 (see also FIG. 10) so that filling with the medium 3 is possible by means of an automatic needle-shaped applicator inserted through the hollow plunger rod and stopper element. After emptying the base body and retracting the plunger rod 18, the stopper element 16 detaches itself from the plunger rod 18 since the plunger rod strikes the stopper element 16 only in the emptying direction and is subsequently released. The injector sleeve 17 envelops the jacket 5 at least in part.

Figure 9:
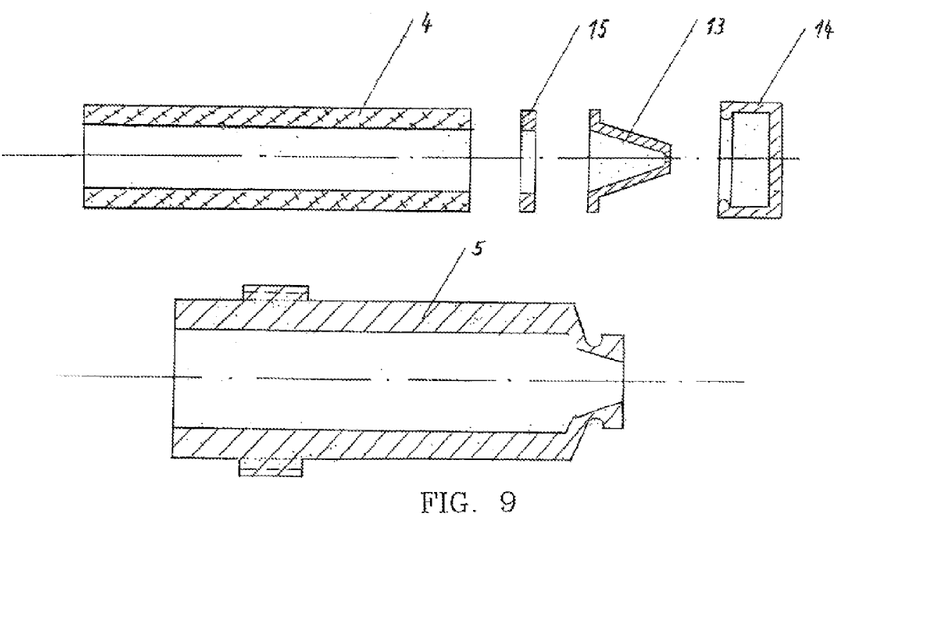
FIG. 9 shows a schematic exploded view through the ampoule unit shown in FIG. 8, and FIG. 10 a to c show a schematic representation of the functional principle of the self-releasing stopper element and the seal of the plunger rod.

FIG. 9 is a schematic representation of the functional principle of the sealing system provided by the interaction of the base body 4, the sealing element 15, the nozzle 13 and the cap 14 in combination with the jacket 5. The sealing system is implemented by the fact that the nozzle 13 clampingly engages in and forms a snug sealing fit on the conically tapering inside portion of the jacket 5 and that the nozzle 13 furthermore interacts with the sealing element 15 and the base body 4.

FIGS. 10a and 10b illustrate the principle by which the plunger rod 18 and the stopper element 16 interact with each other and clearly show that during injection, an anterior part of the plunger rod 18 pushes against a posterior part of the stopper element 16 and is released in the reverse direction.

FIG. 10c shows a hollow plunger rod 18 which has been pinched in two places and which, after filling the base body with a medium, has been sealed by pinching it so that the medium can be stored under sterile conditions.

Finally, the following should be added: The nozzle 13, the elastic sealing element 15 and the base body 4 are assembled by means of the jacket 5, and the cap 14 is subsequently screwed onto the jacket 5. The stopper element 16 and the plunger rod 18 are assembled and subsequently inserted into the base body 4 of the ampoule unit 2. Because of the special construction of the stopper element 16 and the plunger rod 18, all components can be assembled under normal conditions; i.e., no clean room is required. Subsequently, the complete ampoule units can be placed into so-called trays holding 20×20 units, with each tray being wrapped in separate polyethylene bags. A plurality of trays is stacked on a pallet and wrapped again. The entire pallet is subsequently sterilized by means of gamma radiation. In the sterile room, the trays are subsequently removed from the polyethylene bag and transferred to a bottling station, which bottling station fills the ampoule units through the hollow plunger rod and through the stopper elements having the corresponding material recess, in particular and for example openings. Next, the piston road is first pinched in a place A1 farther away from the actual base body 4 and subsequently in a place A2 closer to the base body. Using this method ensures that the content of the ampoule unit is nearly or completely free from gas.

The special feature of the present invention is the fact that pharmaceutical agents can now be stored for a long time (>30 days) in a needle-less injection application system.

The invention claimed is:

1. A needle-free injection device for needle-free injection of a medium, comprising:
   an ampoule unit including
      a main body filled with an injectable substantially gas-free medium,
      a nozzle positioned at an axially longitudinal end of the ampoule unit that defines an outlet for ejecting the medium,
      a jacket completely surrounding the main body in a longitudinal axial direction of the ampoule unit and partially surrounding the nozzle so that the nozzle abuts an inner wall of the jacket in a form-fitting manner, the jacket exerting compressive forces on the main body to at least counterbalance the internal stresses in the main body, and
      a hollow plunger rod through which the main body is able to be filled, the hollow plunger rod including at least one pinched portion that forms a seal to seal the medium within the main body after the main body is filled.

2. The needle-free injection device of claim 1, wherein the jacket exerts forces on the main body that are at least 100% of compressive forces formed during injection of the medium.

3. The needle-free injection device of claim 1, wherein the jacket is at least one of shrink-fitted onto the main body, applied to the main body by a casting process, applied to the main body by polymerization, and press-fitted onto the main body.

4. The needle-free injection device of claim 1, wherein the jacket comprises polyamide, a fiber composite, and/or an MCP alloy.

5. The needle-free injection device according to claim 1, wherein the injector device further comprises an injector sleeve for the needle-free injection of the medium, a spring activation element for driving an activating element for ejecting the medium, wherein the injector device in a spring-loaded state is configured such that, with respect to tension of the spring activation element, only the spring activation element, the activating element, a locking element, and a thrust-bearing device are acted upon by a spring tension force provided by the spring activation element, wherein the injector sleeve is not exposed to the spring tension force because the thrust-bearing device is independent of the injector sleeve, wherein the activating element is tensioned by the spring activation element and releasably securable by a locking element, and forces generated by the spring activation element are absorbed by the thrust-bearing device, the locking element engages the activating element so as to secure the activating element, wherein the locking element comprises a lever and the activating element is secured by an undercut section, wherein a releasing element is tensioned by the spring activation element and actuatable in a direction corresponding to an injection direction the medium is ejected, the activating element is releasable by swiveling or rotating the locking element, wherein the releasing element is substantially wedge-shaped and engages the locking element by moving the releasing element in the injection direction.

6. The needle-free injection device of claim 1, wherein the ampoule unit is mountable to the injection device to bring the injection device into a pre-injection state and is removable from the injection device, at least one of a screw thread and a ring-shaped snap locking connection is configured to removably couple the ampoule unit to the injection device.

7. The needle-free injection device of claim 1, further comprising:

an injector device including a releasing element and a securing element, the securing element configured to secure the releasing element during transportation and/or against unintentional release of the medium from the ampoule unit, the injector device having a groove configured to receive the securing element, wherein the ampoule unit has a longitudinally movable stopper element to seal the ampoule unit and movable to cause the medium to be ejected from the ampoule unit, at least one of a thread and an annular snap-locking connection is provided for mounting or removing the ampoule unit, a cap is configured to cover the outlet, a resilient sealing element is positioned between the main body and the nozzle, the resilient sealing element is made of silicone, the nozzle is made of steel, the nozzle has one or more discharge openings, the nozzle is configured to form a sealing press fit with a nozzle screw joint, the hollow plunger rod is movable to move the stopper element, the stopper element has a material recess corresponding to a hollow region of the plunger rod, the stopper element is configured to be separated from the plunger rod after ejecting the medium when the plunger rod is retracted, and the releasing element is configured to remain in an injector sleeve after actuation of the releasing element.

8. The needle-free injection device of claim 1, further comprising:

an injector device including a releasing element and a securing element, the securing element configured to secure the releasing element during transportation and/or against unintentional release of the medium from the ampoule unit, the injector device having a groove configured to receive the securing element.

\* \* \* \* \*

UNITED STATES PATENT AND TRADEMARK OFFICE
CERTIFICATE OF CORRECTION

| | |
|---|---|
| PATENT NO. | : 8,480,617 B2 |
| APPLICATION NO. | : 12/096740 |
| DATED | : July 9, 2013 |
| INVENTOR(S) | : Lenzner et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 555 days.

Signed and Sealed this
Sixteenth Day of December, 2014

Michelle K. Lee
*Deputy Director of the United States Patent and Trademark Office*